United States Patent
Berkner et al.

(10) Patent No.: US 10,327,627 B2
(45) Date of Patent: Jun. 25, 2019

(54) USE OF PLENOPTIC OTOSCOPE DATA FOR AIDING MEDICAL DIAGNOSIS

(71) Applicants: Kathrin Berkner, Los Altos, CA (US); Lingfei Meng, Redwood City, CA (US); Ivana Tosic, Berkeley, CA (US); Nikhil Balram, Mountain View, CA (US)

(72) Inventors: Kathrin Berkner, Los Altos, CA (US); Lingfei Meng, Redwood City, CA (US); Ivana Tosic, Berkeley, CA (US); Nikhil Balram, Mountain View, CA (US)

(73) Assignee: Ricoh Company, Ltd., Tokyo (JP)

(*) Notice: Subject to any disclaimer, the term of this patent is extended or adjusted under 35 U.S.C. 154(b) by 169 days.

(21) Appl. No.: 14/318,578

(22) Filed: Jun. 28, 2014

(65) Prior Publication Data

US 2014/0316238 A1    Oct. 23, 2014

Related U.S. Application Data

(63) Continuation-in-part of application No. 13/896,924, filed on May 17, 2013, now Pat. No. 9,565,996.
(Continued)

(51) Int. Cl.
*A61B 1/227* (2006.01)
*A61B 1/00* (2006.01)
(Continued)

(52) U.S. Cl.
CPC .......... *A61B 1/227* (2013.01); *A61B 1/00186* (2013.01); *A61B 1/042* (2013.01); *A61B 1/055* (2013.01); *G02B 23/243* (2013.01); *G02B 23/2484* (2013.01); *A61B 1/00009* (2013.01); *A61B 5/0075* (2013.01)

(58) Field of Classification Search
CPC ......... A61B 1/227; A61B 5/6817; A61B 5/00; A61B 1/042; A61B 5/0075; G02B 23/243
See application file for complete search history.

(56) References Cited

U.S. PATENT DOCUMENTS

| 6,110,106 A | 8/2000 | MacKinnon et al. |
| 7,058,441 B2 | 6/2006 | Shahar et al. |

(Continued)

FOREIGN PATENT DOCUMENTS

| JP | 2000-126116 A | 5/2000 |
| JP | 2002-034916 A | 2/2002 |

(Continued)

OTHER PUBLICATIONS

Bedard, N. et al., "Light Field Otoscope," Imaging and Applied Optics 2014, OSA Technical Digest (online), Optical Society of America, 2014, Paper IM3C.6, 4 pages.
(Continued)

*Primary Examiner* — Angela M Hoffa
*Assistant Examiner* — Vani Gupta
(74) *Attorney, Agent, or Firm* — Fenwick & West LLP

(57) ABSTRACT

A plenoptic otoscope captures images used in making a medical diagnosis. For example, the plenoptic data can be processed to produce enhanced imagery of the ear interior, and this enhanced imagery can be used in making a medical diagnosis.

16 Claims, 11 Drawing Sheets
(8 of 11 Drawing Sheet(s) Filed in Color)

Related U.S. Application Data

(60) Provisional application No. 61/754,327, filed on Jan. 18, 2013, provisional application No. 61/946,267, filed on Feb. 28, 2014.

(51) Int. Cl.
    *A61B 1/04*     (2006.01)
    *A61B 1/055*     (2006.01)
    *G02B 23/24*     (2006.01)
    *A61B 5/00*     (2006.01)

(56) References Cited

U.S. PATENT DOCUMENTS

| | | | |
|---|---|---|---|
| 7,399,275 B2 | 7/2008 | Goldfain et al. | |
| 7,399,375 B2 | 7/2008 | Leiser et al. | |
| 7,433,042 B1 | 10/2008 | Cavanaugh et al. | |
| 7,448,753 B1 | 11/2008 | Chinnock | |
| 7,544,163 B2 | 6/2009 | MacKinnon et al. | |
| 7,723,662 B2 | 5/2010 | Levoy et al. | |
| 7,901,351 B2 | 3/2011 | Prescott | |
| 7,936,392 B2 | 5/2011 | Ng et al. | |
| 7,995,214 B2 | 8/2011 | Forster et al. | |
| 8,066,634 B2 | 11/2011 | Andreassen et al. | |
| 8,100,826 B2 | 1/2012 | MacKinnon et al. | |
| 8,107,086 B2 * | 1/2012 | Hart | A61B 1/043 356/2 |
| 8,143,565 B2 | 3/2012 | Berkner et al. | |
| 8,617,061 B2 | 12/2013 | Magalhaes Mendes et al. | |
| 8,824,779 B1 * | 9/2014 | Smyth | G06K 9/0061 382/100 |
| 8,845,526 B2 * | 9/2014 | Hart | A61B 1/00082 356/626 |
| 8,944,596 B2 | 2/2015 | Wood et al. | |
| 8,949,078 B2 | 2/2015 | Berkner et al. | |
| 9,001,326 B2 * | 4/2015 | Goldfain | G01J 3/0224 356/237.2 |
| 9,565,993 B2 | 2/2017 | Berkner et al. | |
| 2005/0228231 A1 | 10/2005 | MacKinnon et al. | |
| 2008/0259274 A1 | 10/2008 | Chinnock | |
| 2010/0004513 A1 | 1/2010 | MacKinnon et al. | |
| 2011/0026037 A1 | 2/2011 | Forster et al. | |
| 2011/0152621 A1 | 6/2011 | Magalhaes Mendes et al. | |
| 2012/0065473 A1 | 3/2012 | Andreassen et al. | |
| 2012/0182438 A1 | 7/2012 | Berkner et al. | |
| 2012/0226480 A1 | 9/2012 | Berkner et al. | |
| 2012/0320340 A1 | 12/2012 | Coleman, III | |
| 2012/0327426 A1 | 12/2012 | Hart et al. | |
| 2012/0327427 A1 | 12/2012 | Hart et al. | |
| 2013/0002426 A1 | 1/2013 | Hart et al. | |
| 2013/0002824 A1 | 1/2013 | Hart et al. | |
| 2013/0003078 A1 | 1/2013 | Hart et al. | |
| 2013/0027516 A1 | 1/2013 | Hart et al. | |
| 2013/0128223 A1 | 5/2013 | Wood et al. | |
| 2013/0237754 A1 | 9/2013 | Berglund et al. | |
| 2013/0289353 A1 | 10/2013 | Seth et al. | |
| 2014/0012141 A1 | 1/2014 | Kim et al. | |
| 2014/0192255 A1 | 7/2014 | Shroff et al. | |
| 2014/0316238 A1 | 10/2014 | Berkner et al. | |
| 2014/0350379 A1 | 11/2014 | Verdooner | |
| 2015/0005640 A1 | 1/2015 | Davis et al. | |
| 2015/0005644 A1 | 1/2015 | Rhoads | |
| 2015/0116526 A1 | 4/2015 | Meng et al. | |
| 2015/0117756 A1 | 4/2015 | Tosic et al. | |
| 2015/0126810 A1 | 5/2015 | Wood et al. | |

FOREIGN PATENT DOCUMENTS

| | | |
|---|---|---|
| JP | 2007-004471 A | 1/2007 |
| JP | 2007-500541 A | 1/2007 |
| JP | 2009-244429 A | 10/2009 |
| JP | 2014-138858 A | 7/2014 |
| JP | 2014-530697 A | 11/2014 |
| WO | WO 2012/058641 A2 | 5/2012 |
| WO | WO 2012/066741 A1 | 5/2012 |
| WO | WO 2013/138081 A1 | 9/2013 |
| WO | WO 2014/021994 A1 | 2/2014 |

OTHER PUBLICATIONS

Bedard, N. et al., "In Vivo Middle Ear Imaging with a Light Field Otoscope," Optics in the Life Sciences, OSA Technical Digest, (online), Optical Society of America, Paper BW3A.3, 3 pages.

Berkner, K. et al., "Measuring Color and Shape Characteristics of Objects from Light Fields," Imaging and Applied Optics, 2015, 3 pages.

Cho, N.H. et al., "Optical Coherence Tomography for the Diagnosis of Human Otitis Media," Proc. SPIE, 2013; 5 pages, vol. 8879, 88790N.

Hernandez-Montes, M.S. et al., "Optoelectronic Holographic Otoscope for Measurement of Nanodisplacements in Tympanic Membranes," Journal of Biomedical Optics, Proceedins of the XIth International Congress and Exposition, Society for Experimental Mechanics Inc., Jun. 2-5, 2008, 7 pages, vol. 14, No. 3.

Kim, C. et al., "Scene Reconstruction from High Spatio-Angular Resolution Light Fields," Transactions on Graphics (TOG), 2013, 11 pages, vol. 32, No. 4.

Kubota A. et al.,"View Interpolation using Defocused Multi-View Images," Proceedings of APSIPA Annual Summit and Conference, Asia-Pacific Signal and Information Processing Association, 2009 Annual Summit and Conference, Saporo, Japan, Oct. 4, 2009, pp. 358-362.

Kuruvilla, A. et al., "Otitis Media Vocabulary and Grammar," CMU, ICIP, 2012, 4 pages.

Levoy, M. "Light Field and Computational Imaging," IEEE Computer Magazine, 2006, pp. 46-55, vol. 39.

Levoy, M. et al., "Light Field Microscopy," Proc. SIGGRAPH, ACM Transactions on Graphics, 2006, pp. 1-11, vol. 25, No. 3.

Ng, R. et al., "Light Field Photography with a Hand-Held Plenoptic Camera," Stanford Tech Report, 2005, pp. 1-11.

Sundberg, M., et al., "Fibre Optic Array for Curvature Assessment—Application in Otitis Media," Medical & Biological Engineering & Computing, Mar. 2004, pp. 245-252, vol. 42, No. 2.

Sundberg, M., et al., "Diffuse Reflectance Spectroscopy of the Human Tympanic Membrane in Otitis Media, "Physiological Measurement, 2004, pp. 1473-93, vol. 25, No. 6.

Tao, M. et al., "Depth from Combining Defocus and Correspondence Using Light-Field Cameras," in Proceedings of the International Conference on Computer Vision, 2013, 8 pages.

Wanner, S. et al., "Globally Consistent Depth Labeling of 4D Light Fields," in Proceedings of the IEEE Computer Society Conference on Computer Vision and Pattern Recognition, 2012, pp. 41-48.

Yang, T. et al., "High Performance Imaging Through Occlusion via Energy Minimization-Based Optimal Camera Selection," International Journal of Advanced Robotic Systems, 2013, pp. 19, vol. 10.

U.S. Appl. No. 14/312,586, Lingfei Meng et al., filed Jun. 23, 2014, [Copy not enclosed].

United States Office Action, U.S. Appl. No. 13/896,924, dated Jul. 8, 2015, 15 pages.

Japanese Office Action, Japanese Application No. 2016-211050, dated Sep. 26, 2017, 5 pages (with concise explanation of relevance).

Japanese Office Action, Japanese Application No. 2014-006668, dated Sep. 26, 2017, 4 pages (with concise explanation of relevance).

\* cited by examiner

USE OF PLENOPTIC OTOSCOPE DATA FOR AIDING MEDICAL DIAGNOSIS

CROSS-REFERENCE TO RELATED APPLICATION

This application is a continuation-in-part of U.S. patent application Ser. No. 13/896,924, "Plenoptic Otoscope," filed May 17, 2013; which claims priority under 35 U.S.C. § 119(e) to U.S. Provisional Patent Application Ser. No. 61/754,327, titled "Plenoptic Otoscope," filed Jan. 18, 2013. This application also claims priority under 35 U.S.C. § 119(e) to U.S. Provisional Patent Application Ser. No. 61/946,267, "Use of Lightfield Otoscope Data for Aiding Medical Diagnosis," filed Feb. 28, 2014. The subject matter of all of the foregoing are incorporated herein by reference in their entirety.

BACKGROUND OF THE INVENTION

1. Field of the Invention

This invention relates generally to otoscopes for imaging the interior of human or animal ears.

2. Description of the Related Art

Imaging inside of the human or animal ear is a common task for doctors. Typically a doctor uses an otoscope to look inside the ear of the patient. Such an exam is common procedure when trying to diagnose ear infections. Most doctors use a manual otoscope, which is simply a magnifier combined with an illuminator. The image that the doctor sees exists only in the doctor's memory. Therefore, comparing different images looked at different times is difficult and not objective.

There exist digital otoscopes that have a digital camera embedded in the otoscope or at the end of a fiber-optic cable that guides the light from the instrument head to an external module. The digital data are then viewed on an external display. Such digital otoscopes are marketed as solutions for telemedicine applications. Cameras currently used in digital otoscope consist of conventional imaging optics and sensors. With the rapid development of mobile platforms for smart healthcare applications, attachments for cell phones are being developed that allow the imaging of the inside of an ear with a smartphone for illumination, image capture, and display.

The features that doctors analyze when trying to make a diagnosis for ear inflammation ("otitis media") include features such as bulging of the ear drum, translucency, and yellowness of tissue. However, these features are difficult to analyze from flat two-dimensional images taken by conventional cameras. Conventional otoscopes do not explicitly obtain three-dimensional (i.e., depth) information or wavelength-dependent characteristics. They are limited to images of a single focal plane inside the ear canal. Moreover, often objects such as wax or hair can obstruct the view onto the tympanic membrane (TM) or other objects of interest and must be removed before taking a picture of the TM, requiring some extra procedures before an otoscope can be used.

Therefore, there exists a need for improved data acquisition to allow the extraction of three dimensions and color features more reliably.

SUMMARY OF THE INVENTION

The present invention overcomes the limitations of the prior art by providing a plenoptic otoscope. A plenoptic otoscope can be designed to provide good quality data for feature extraction for otitis diagnosis. In one implementation, a plenoptic sensor and an optional filter module are combined with a conventional digital otoscope to create a plenoptic otoscope. With these additions, three-dimensional (3D) shapes, translucency and/or color information can be captured.

In one embodiment, a plenoptic otoscope includes a primary imaging system and a plenoptic sensor. The primary imaging system is characterized by a pupil plane, and includes an otoscope objective and relay optics, which cooperate to form an image of the inside of an ear at an intermediate image plane. The plenoptic sensor includes a microimaging array positioned at the intermediate image plane and a sensor array positioned at a conjugate of the pupil plane.

In one implementation, a plenoptic otoscope further includes a filter module positioned at a pupil plane conjugate (i.e., at the pupil plane or one of its conjugates). In one approach, the filter module is located in a detachable tip, and is positioned at an entrance pupil of the primary imaging system when the detachable tip is attached to the otoscope. In this way, different filter modules can be included in detachable tips, and the filter modules can be switched in and out of the plenoptic otoscope by switching detachable tips.

In another implementation, a plenoptic otoscope is operable in a depth imaging mode. In the depth imaging mode, a plenoptic image (also referred to as plenoptic data) captured by the sensor array is processed to provide a three-dimensional depth image of an inside of an ear. Alternately or additionally, a plenoptic otoscope is operable in a spectral imaging mode. In the spectral imaging mode, plenoptic data captured by the sensor array is processed to provide two or more different spectral images of an inside of an ear. Disparity or depth maps can also be determined. The plenoptic otoscope may be switchable between the depth imaging mode and the spectral imaging mode.

Another aspect relates to the use of the data captured by the plenoptic otoscope to assist in making a medical diagnosis. For example, the plenoptic data can be processed to produce enhanced imagery of the ear interior. Data based on the enhanced imagery can then be used to assist a person in making a medical diagnosis. This diagnostic data could be the enhanced imagery itself or it could involve further processing of the enhanced imagery. Alternately, the diagnosis can be made automatically by a computer system, for example by a classifier trained on prior data.

Enhanced imagery of the tympanic membrane is a good example. A plenoptic otoscope can simultaneously capture depth and spectral information about the tympanic membrane. A depth map of the tympanic membrane can produce information regarding its shape—whether it is bulging or retracting, and the estimated curvature. Spectral information can include an amber or yellow image, which is especially useful to diagnose conditions of the tympanic membrane. Many diagnoses are based on shape, color and/or translucency, which can all be captured simultaneously by a plenoptic otoscope.

Plenoptic data also includes multiple views of the same image. This allows the user to refocus to different depths in the image and to view the same image from different viewpoints. For example, the effect of occluding objects may be reduced by taking advantage of multiviews. This could be accomplished by refocusing. Alternately, it could be accomplished by segmenting the light field (multiple views) into depth layers.

Examples of diagnostic data that are not images but are derived from enhanced imagery, include classification of the tympanic membrane as bulging, retracting or neutral, estimated curvature of the tympanic membrane, estimated color of the tympanic membrane, and features and feature vectors reflecting any of the foregoing.

Other aspects of the invention include methods, devices, systems, and applications related to the approaches described above and its variants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention has other advantages and features which will be more readily apparent from the following detailed description of the invention and the appended claims, when taken in conjunction with the accompanying drawings, in which:

Figure 1A:
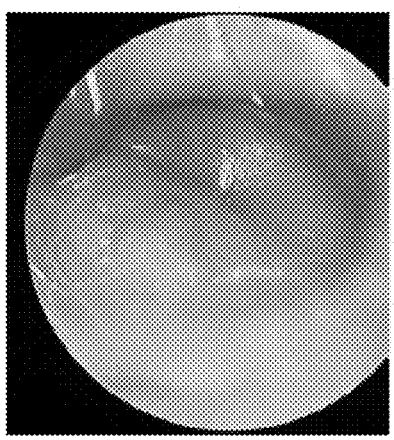
FIGS. 1a-c (prior art) are example images showing different conditions of the ear as well as features to distinguish the conditions.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed. To facilitate understanding, identical reference numerals have been used where possible, to designate identical elements that are common to the figures.

A plenoptic otoscope design can overcome the poor data quality of current otoscopes for feature extraction for otitis diagnosis. In one implementation, a plenoptic sensor is added to a conventional digital otoscope as well as an optional filter module inside the otoscopic instrument. With these additions, three-dimensional (3D) shapes, translucency, and/or detailed color information can be captured. This data and possibly other data captured by a plenoptic otoscope can be used to aid in medical diagnosis of a patient's ear.

Figure 1B:
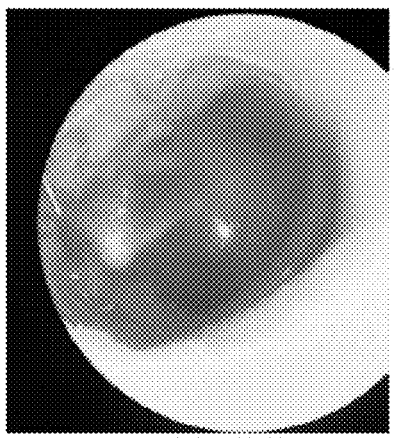
Figure 1C:
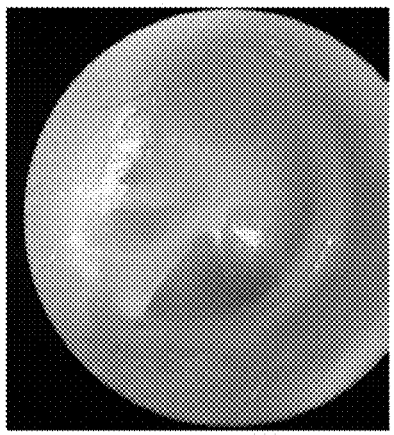

FIGS. 1a-c (prior art) are example images showing different conditions of the ear as well as features to distinguish the conditions. The three conditions shown are acute otitis media (AOM) in FIG. 1a, otitis media with effusion (OME) in FIG. 1b, and otitis media with no effusion (NOE) in FIG. 1c. Table 1 lists some features distinguishing the conditions. More specifically, Table 1 lists otoscopic findings on tympanic membrane (TM) images associated with the above three conditions.

TABLE 1

Otoscopic findings associated with clinical diagnostic categories on TM images

|  | AOM | OME | NOE |
|---|---|---|---|
| Color | White, pale yellow, markedly red | White, amber, gray, blue | Gray, pink |
| Position | Distinctly full, bulging | Neutral, retracted | Neutral, retracted |
| Translucency | Opacified | Opacified, semi-opacified | Translucent |

As can be seen from FIGS. 1a-c and Table 1, the three conditions of the ear are different and they can be distinguished from one another based on one or more of the following features: color, position (e.g., 3D shape), and translucency. In order to make correct diagnosis of the ear condition, otoscopic images capturing accurate information about color, 3D shape and translucency of an inside of an ear (e.g., a tympanic membrane in an ear canal) are desirable.

Figure 2:
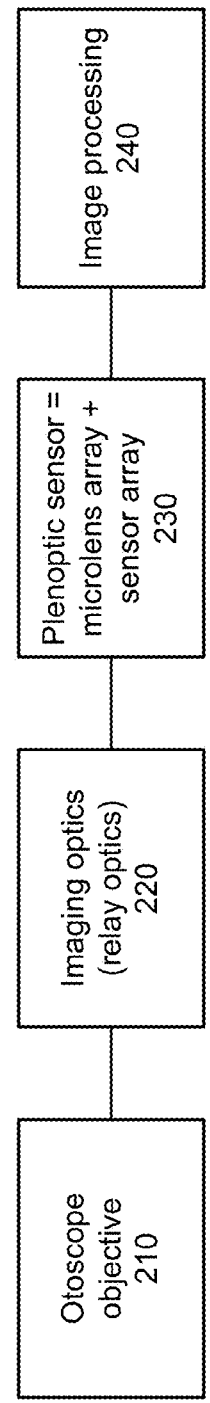
FIG. 2 is a block diagram of a plenoptic digital otoscope system.

FIG. 2 is a block diagram of a plenoptic digital otoscope system. The system includes an otoscope objective 210, imaging optics (relay optics) 220, a plenoptic sensor 230 and image processing 240. The otoscope objective 210 can be an imaging objective, as used in conventional otoscopes. The imaging optics 220 works in conjunction with the otoscope objective 210 to form a conventional image within the otoscope instrument. Rather than a conventional sensor array capturing this image, a plenoptic sensor 230 captures the image. The plenoptic sensor 230 is a sensor array with a microimaging array (e.g., a microlens array or pinhole array) mounted in front of it. In addition, a filter module (not shown in FIG. 2) can be inserted at a pupil plane of the optical train (or at one of its conjugates) to allow spectral or other filtering of the light. The digital information extracted by the plenoptic sensor 230 is sent to a computing module 240 that performs the image processing of the plenoptic data. In this way, three-dimensional and/or spectral data can be extracted.

The plenoptic otoscope head can be mounted on top of a handle that houses an illumination source (e.g., portable system) or can be connected to an illumination source (e.g., wall-mounted system). Such an illumination source may be an LED light source, a standard white illumination source, etc. The illumination source may have polarization characteristics as well. For example, it may emit unpolarized, partially polarized, or completely polarized (e.g., TE, TM) light.

Figure 3:
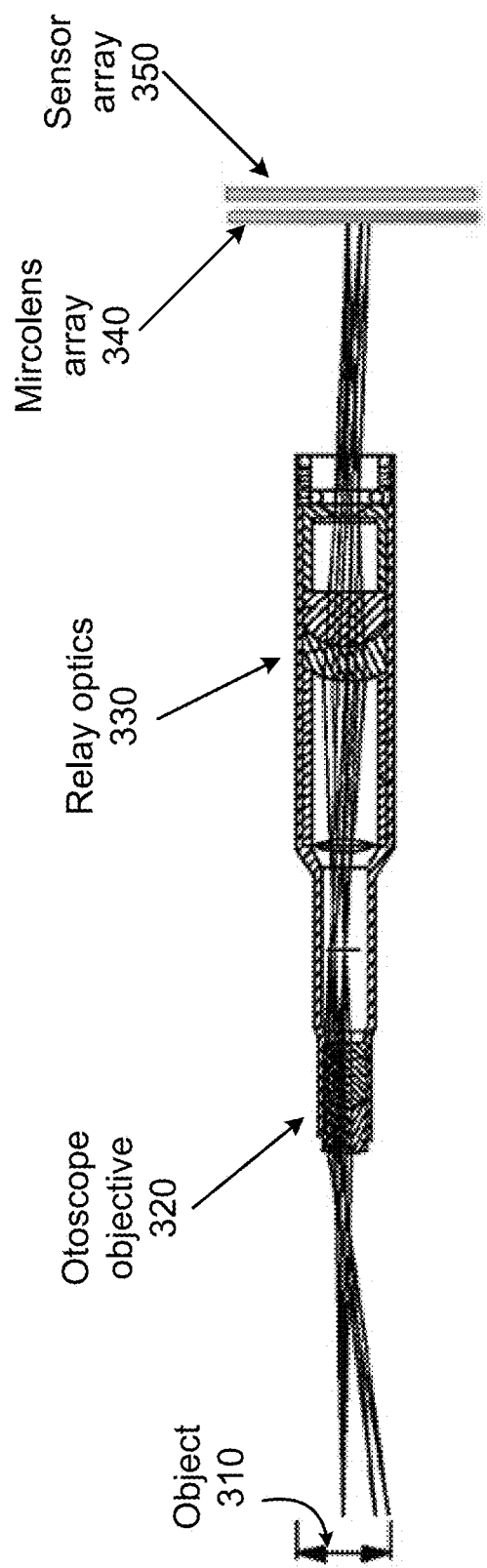
FIG. 3 shows an optical train of a plenoptic otoscope.

FIG. 3 shows an optical train of a plenoptic otoscope. The plenoptic otoscope includes two parts: a primary imaging system and a plenoptic sensor. The primary imaging system includes an otoscope objective 320 and relay optics 330. They cooperate to form a conventional image of an object 310 (e.g., an inside of an ear, a tympanic membrane, etc.). A plenoptic sensor (a microlens array 340 and a sensor array 350) is positioned so that the microlens array 340 is located in the conventional image plane, which is an intermediate image plane of the primary imaging system. The sensor array 350 then captures lightfield data (or plenoptic data), which will be referred to as the plenoptic image of the object 310.

In one embodiment, the plenoptic image contains depth data. A computing module (not shown in FIG. 3) further processes the captured plenoptic image to produce three-dimensional data. This operational mode of the plenoptic otoscope may be referred to as a depth imaging mode. For example, in the depth imaging mode, the plenoptic data captured by the sensor array 350 may be processed to provide a three-dimensional depth image of an inside of an ear.

Figure 4A:
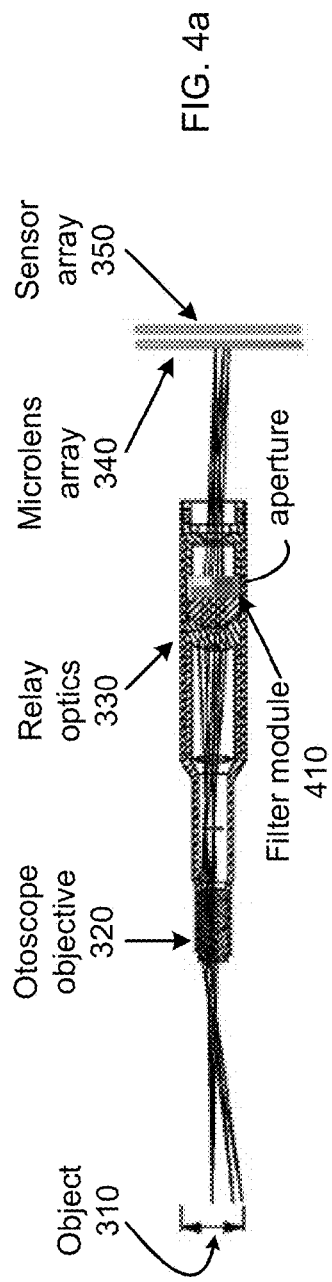
FIGS. 4a-c show optical trains of a plenoptic otoscope with filtering.
Figure 4B:
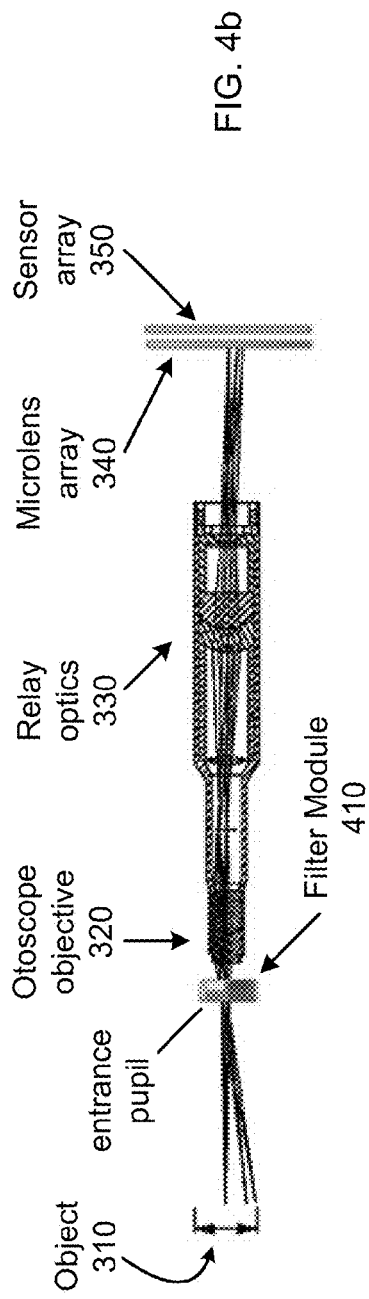
Figure 4C:
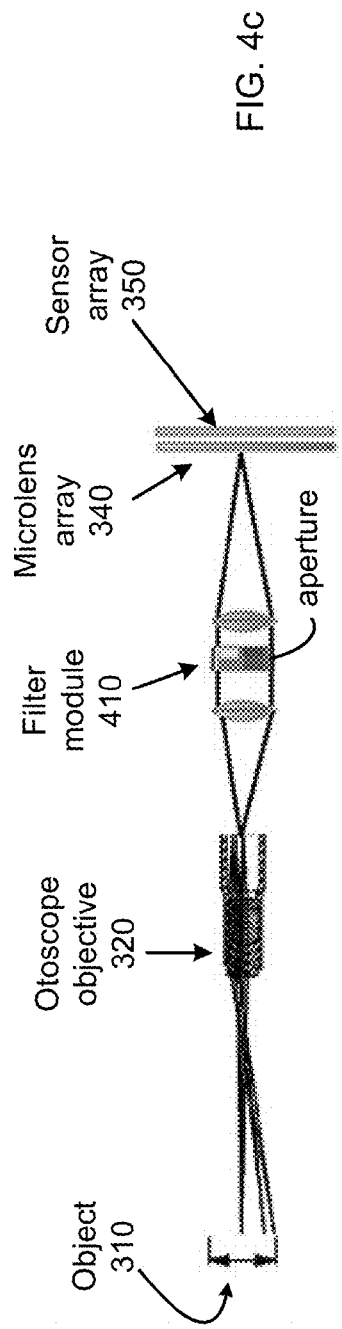

Another possible operational mode of the plenoptic otoscope is a spectral imaging mode. In the spectral imaging mode, the plenoptic image captured by the sensor array 350 contains spectral information and may be processed to provide two or more different spectral images of the object 310. In one embodiment, spectral imaging can be enabled by placing a filter module at a pupil plane conjugate of the plenoptic otoscope, as shown in FIGS. 4a-c. The term "pupil plane conjugate" is used to refer to any plane that is a pupil plane of the primary imaging system or a conjugate plane of that pupil plane. For example, the term pupil plane conjugate includes the entrance pupil plane and the exit pupil plane of the primary imaging system.

FIGS. 4a-c show different placements of the filter module. In FIG. 4a, the filter module 410 is located at an aperture between the relay optics and the plenoptic sensor. In FIG. 4b, the filter module 410 is located at the entrance pupil. In FIG. 4c, the filter module 410 is located at an aperture between a pair of relay lenses. In each of the embodiments shown in FIGS. 4a-c, the filter module 410 is positioned at a pupil plane conjugate.

In one implementation of FIG. 4b, the filter module is contained in a detachable tip (or ring), which is attached to the plenoptic otoscope. When the tip is attached, the filter module is positioned at the entrance pupil of the first lens group, as shown in FIG. 4b. As in a conventional otoscope, a speculum used to enter the ear canal may be attached to the detachable tip.

In one embodiment, the plenoptic otoscope is switchable between the depth imaging mode and the spectral imaging mode. In one approach, a clear filter is used for the depth imaging mode and one or more different spectral filters are used for the spectral imaging mode. To switch between the two modes, the filter module 410 could include one section that is clear and another section that contains the spectral filters. The filter module could be translated relative to the primary imaging system, so that the appropriate section is illuminated. An example of this type of filter module is shown in FIG. 5. This filter module could be positioned in a pupil plane conjugate and translated within the pupil plane conjugate to switch between the set of spectral filters and the clear filter. In FIG. 5, the black circle shows the cross-section of the light traveling through the otoscope.

Figure 5A:
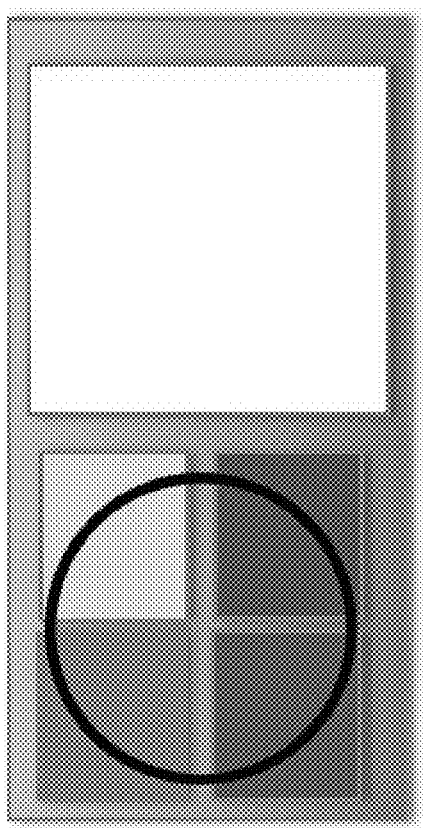
FIGS. 5a-b show use of a filter module with different spectral filters.

In FIG. 5a, the light travels through the spectral filters, which are depicted as a red rectangle, a blue rectangle, a green rectangle, and a yellow rectangle. The portion of light that passes through a color filter forms an image of the object (within the plenoptic image) that has been filtered by the corresponding color filter. As a result, spectral imaging is enabled. In this example, a plenoptic image is formed, from which four different spectral images of the object (i.e., a red image, a blue image, a green image, and a yellow image) may be extracted.

Figure 5B:
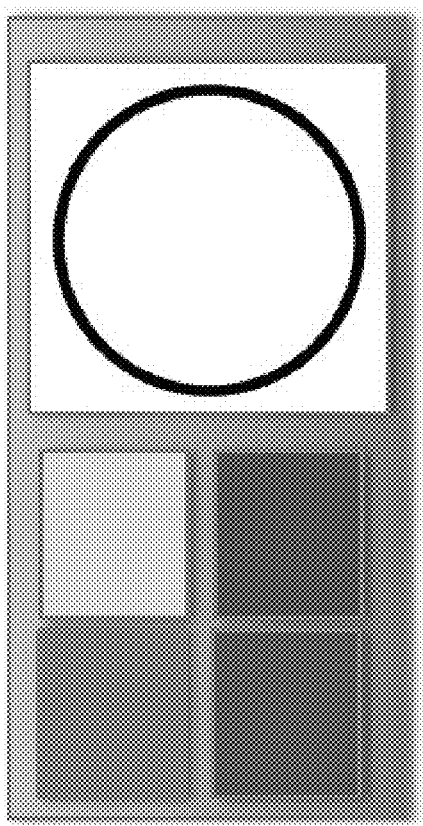

In FIG. 5b, the filter module is translated relative to the primary imaging system so that the light travels through the clear aperture. This might be used for depth imaging, for example. In this example, a plenoptic image is formed, from which a three-dimensional depth image may be extracted.

This particular filter module has RGB filters for color imaging, plus a yellow filter since yellowish or amber color of tissue is an indicator, and is only shown as an example. In one embodiment, the filter module may include a plurality of different spectral filters. Filters having different colors and/or layouts may also be used in the filter module. For example, see U.S. patent application Ser. No. 13/040,809, filed on May 4, 2011, which is hereby incorporated by reference in its entirety.

Spectral imaging is useful to help distinguish different ear conditions. Some of the ear conditions are shown in FIGS. 1a-c and also in Table 1. For example, AOM is markedly red, OME features amber, and NOE contains gray and pink. In one embodiment, the filter module includes different filters selected to distinguish different ear conditions. Such a filter module is shown in FIGS. 5a-b, e.g., the filter module containing red-green-blue filters and a yellow filter.

Figure 6A:
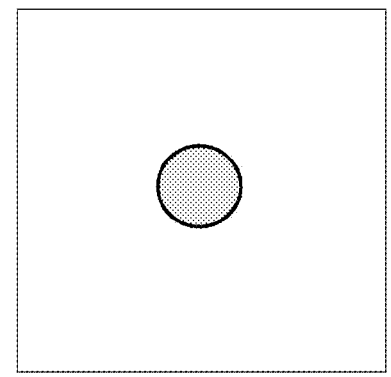
FIGS. 6a-c show additional filter modules.
Figure 6B:
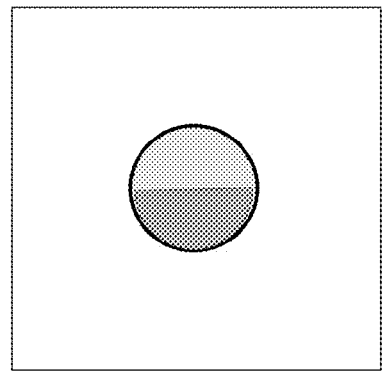
Figure 6C:
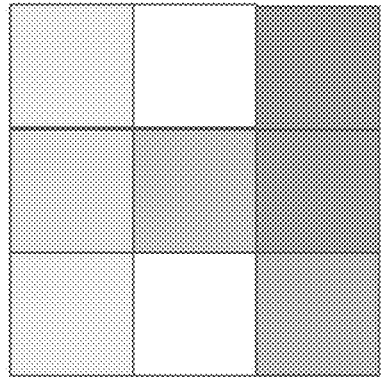

FIGS. 6a-c show some additional filter modules. In FIG. 6a, the filter module has a yellow filter and a transparent area. In FIG. 6b, the filter module has a yellow filter, an amber filter and a transparent area. The sensor array can also be fitted with spectral filters, such as a standard Bayer RGB pattern. Thus, when the filter modules in FIG. 6a or 6b are used with their transparent areas, the Bayer RGB pattern may be used to achieve color imaging. The yellow and amber filters in FIG. 6a and FIG. 6b can be used to extract extra color information. They can be used together with monochromatic sensors and/or RGB sensors (e.g., sensors fitted with a standard Bayer RGB pattern). Such extra color information (e.g., yellow, amber, etc.) can be used to distinguish different ear conditions.

FIG. 6c has an array of filters. The center stripe includes three spectral filters: yellow, amber and a third spectral filter. These can be used for spectral imaging. The top right and top left filters are polarization filters, for example to reduce reflections. The polarization filters may also be useful in extracting illumination characteristics (e.g., when the illumination light has a certain degree of polarization). The middle right and middle left filters are transparent, for example for use in extracting depth information (e.g., depth imaging). The bottom right and bottom left filters are neutral density filters of different densities, for example to increase the dynamic range of the plenoptic otoscope.

Figures 7, 8:
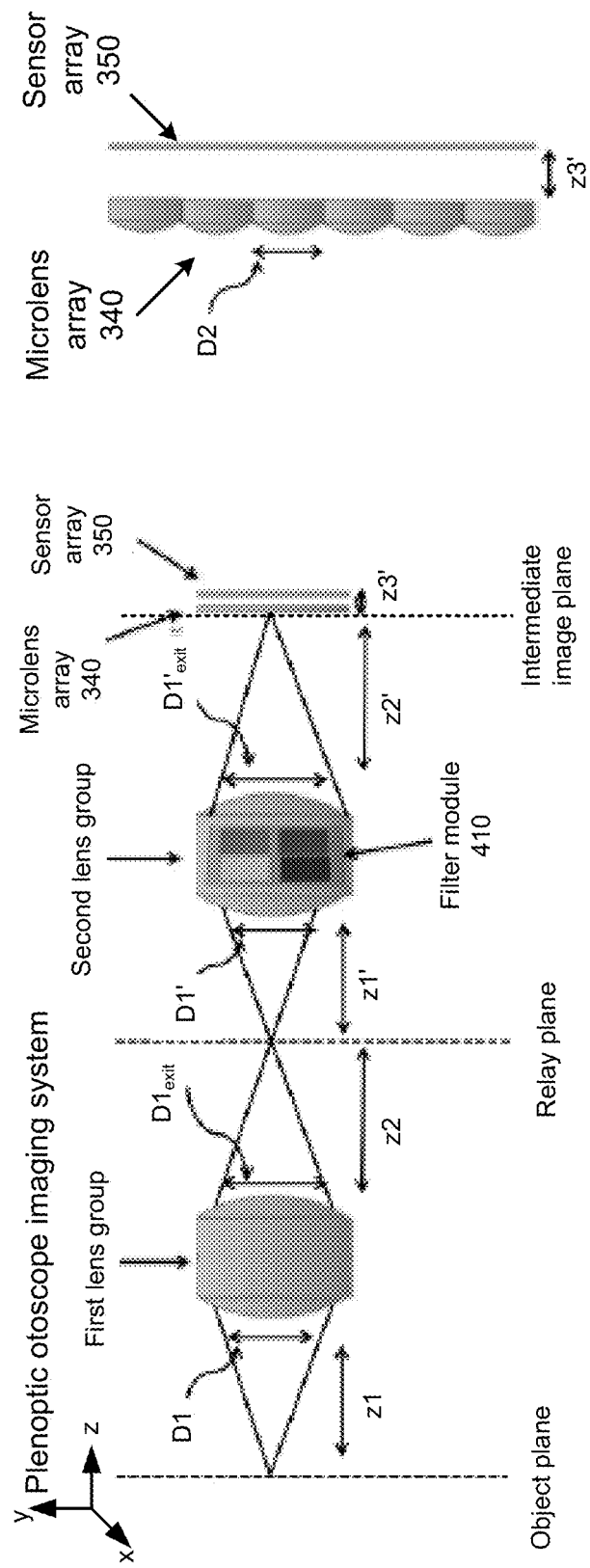
FIGS. 7-8 show a plenoptic otoscope system, introducing notations of dimensions.

FIGS. 7-8 show a plenoptic otoscope system, introducing notation that will be used to describe different design considerations. FIG. 7 depicts a typical embodiment of a plenoptic otoscope, which includes a primary imaging system and a plenoptic sensor. The primary imaging system includes two lens groups. The first lens group is the otoscope objective, and the second lens group is the relay optics. The plenoptic sensor includes a microimaging array 340 and a sensor array 350. In FIG. 8, the microimaging array is a microlens array 340, with each microlens having identical optical properties, such as diameter, radius of curvature, material, and thickness. In one embodiment, the diameter of a microlens is chosen to be between 10 and 100 micron.

As shown in FIG. 7, the object (e.g., a tympanic membrane) is located in an object plane. It is imaged by the first lens group onto a first intermediate image plane (which may be referred to as the relay plane), and then imaged by the second lens group onto a second intermediate image plane where the microlens array 340 is positioned.

In many conventional otoscopes, the magnification of the primary imaging system is set such that the entire tympanic membrane (TM) can be imaged onto the sensor array 350 (as seen in FIGS. 1a-c). Suppose the sensor array 350 has a width W and a height H, and the diameter of the TM is h, then the magnification of the primary imaging system is given by M=min(W,H)/h, where min(x,y) returns the lesser value of x and y.

The average diameter for the TM of an adult is h=7 mm. Here we define optical system specifications for the example of a ⅓" sensor array with width W=4.6 mm and height H=3.7 mm. For this sensor array, the magnification for the primary imaging system is given by M=3.7 mm/7 mm=0.53. Such a magnification is typical for a conventional otoscope. In contrast, a microscope typically has a much larger magnification (>20), and a consumer camera imaging people or natural scenes typically has a much smaller magnification.

The total magnification of the primary imaging system is M=M1*M2, where M1 is the magnification of the first lens group, and M2 is the magnification of the second lens group. For illustration purposes, assume M2=1. In other approaches, M2 can be any suitable number other than 1. In the example where M2=1, M1=M. The working F-number, $N_w$, of the first lens group with magnification M is defined as $N_w=(1+M)N$, where N is the F-number of the primary imaging system (i.e., N=f/D1, where D1 is the diameter of the entrance pupil of the primary imaging system, and f is the effective focal length of the primary imaging system.). In one embodiment, the primary imaging system of the plenoptic otoscope is faster than F/8.

The working distance, z1, for the otoscope is the distance between the object and the first lens group. For imaging a TM, a typical working distance is 27-30 mm. The bones behind the TM are located approximately up to a distance of 15 mm from the TM. As a result, the working distance may vary, for example, from 27 mm up to 45 mm. For illustration purposes, assume the working distance z1=30 mm. The entrance pupil is located in the narrow tip of the otoscope close to the first lens group, and is generally smaller than the tip of the otoscope. The tip of an otoscope has a typical diameter of 4-5 mm in order to fit into an ear canal. Let's assume the entrance pupil to have a diameter of 2 mm. Then the effective focal length of the first lens group is f=N*D1=10.4 mm. The second lens group relays the image of the first lens group onto an intermediate image plane, where the microlens array 340 is positioned. The sensor array 350 is positioned at a distance z3' behind the microlens array 340 to capture the plenoptic image.

In one embodiment, the object is located near the hyperfocal distance of the first lens group. The hyperfocal distance is a distance beyond which all objects can be brought into an acceptable focus. Mathematically, the hyperfocal distance may be expressed as $p=f^2/(N c)+f$, where f is the effective focal length, N is the F-number, and c is the circle of confusion diameter limit. In one implementation, the numerical aperture of a microlens matches the image-side numerical aperture of the primary imaging system. That means the working F-number of the primary imaging system matches the F-number of the microlens. Furthermore, the distance z3' is chosen to be equal to the focal length of the microlens. In this configuration, the depth of field is bounded only in one direction, and therefore may be particularly suitable for imaging distant objects.

In one embodiment, the object is placed at a distance z1 away from the entrance pupil of the first lens group. The distance z2 between the exit pupil of the first lens group and the relay plane is determined by the lens equation as: z2=1/(1/f1−1/z1), where f1 is the effective focal length of the first lens group.

The relationship between the first lens group and the second lens group is given by $D1_{exit}/D1'=z2/z1'$, where $D1_{exit}$ is the diameter of the exit pupil of the first lens group, D1' is the diameter of the entrance pupil of the second lens group, and z1' is the distance between the relay plane and the entrance pupil of the second lens group.

The distance z2' between the exit pupil of the second lens group and the intermediate image plane is determined by the lens equation as: z2'=1/(1/f1'−1/z1'), where f1' is the effective focal length of the second lens group.

The distance z3' between the microlens array and the sensor array is chosen such that $z3'=z2'M_{microlens}$. Here $M_{microlens}$=D2/D1' exit is the magnification of the microlens sub-system, where D2 is the diameter of the microlens (as shown in FIG. 8) and $D1'_{exit}$ is the diameter of the exit pupil of the second lens group. This configuration is specific to imaging with a depth of field bounded in both directions, where the object may not be located near the hyperfocal distance. In comparison, a microscope typically has a much larger magnification (>20), a larger F-number (>15), and a much smaller working distance (a few millimeters).

In one embodiment, the filter module 410 is inserted at the aperture of the second lens group, as depicted in FIG. 7. The filter module 410 is adjustable in such a way that it can be translated laterally in the x-y plane, which is perpendicular to the optical axis (z axis) of the second lens group. For clarity, the coordinate system is also shown in FIG. 7. Furthermore, the second lens group may have a diaphragm/iris/shutter attached to the front/back of the filter module 410. This configuration may permit adjustment of the aperture diameter by opening and closing the diaphragm/iris/shutter.

Switching between depth imaging mode and spectral imaging mode may be accompanied by a change in the depth of field for the primary imaging system (in addition to changing filters). One way to change the depth of field is by adjusting the aperture size. For example, a larger aperture results in a shorter depth of field, which may benefit depth imaging due to the finer depth resolution. On the other hand, a smaller aperture results in a longer depth of field, which may be unsuitable for depth imaging but appropriate for spectral imaging.

In one embodiment, switching between depth and spectral imaging includes opening and closing the diaphragm/iris/shutter at the aperture plane of the second lens group. Two example configurations are given below. In the first configuration, with the effective focal length f=10 mm and a circle of confusion diameter of 0.019 mm, the aperture is wide open to enable a small F-number (e.g., F/5) and a small depth of field (<2 mm). This configuration is suitable for depth imaging or perhaps for combined depth+spectral imaging. In the second configuration, with the effective focal length f=10 mm and a circle of confusion diameter of 0.019 mm, the aperture is stopped down to enable a large F-number (e.g., F/16) and a large depth of field (>3.5 mm). This configuration may be suitable for spectral imaging only.

Switching between depth imaging mode and spectral imaging mode may also be accompanied by a change in focus for the primary imaging system. This may be done via a focusing mechanism. Such a focusing mechanism (e.g., a focusing ring) may move lenses in the primary imaging system and/or move the plenoptic sensor, so that objects at various distances can be focused onto the microlens array plane (i.e., the intermediate image plane). In one approach, the focusing mechanism is adjusted such that a region between 4-5 mm in front of the TM and up to 15 mm behind the TM can be imaged in focus onto the microlens array plane. This may enable different combinations of spectral and/or depth imaging at different regions of interest. For example, it may be desirable to have both depth and spectral imaging for a region near the TM (e.g., to fully distinguish the different ear conditions), while spectral imaging may be enough for other regions. By adjusting the focus, it is possible to select which portion of the ear canal should "receive more attention." For instance, one can adjust the focus with a fine step size (i.e., a fine depth resolution) near the TM to increase the 3D depth information for that region of interest, and adjust the focus with a coarse step size for other regions of the ear canal.

In one embodiment, the plenoptic otoscope is in the spectral imaging mode when the primary imaging system has a depth of field >5 mm. This is useful, for example, for imaging both the TM and the bones behind the TM in focus onto the microlens array plane. Conversely, the plenoptic otoscope is in the depth imaging mode when the primary imaging system has a depth of field <5 mm. In this mode, depth estimation of the TM is possible, for example, by focusing on the bones behind the TM and/or the narrow part of the ear canal in front of the TM. Illustratively, the first lens group may have a working distance up to 45 mm (about 15 mm behind the TM).

In a plenoptic otoscope, it is also possible to include a view finder to enable the examiner to view an image through the view finder of the otoscope at the time of image capture. A beam splitter or a single lens reflex can be used to split the optical path and direct the image to the plenoptic sensor and to the view finder. For example, either a single lens reflex or a beam splitter may be inserted at the relay plane between the first lens group and the second lens group of an otoscope (as shown in FIG. 7) to allow a medical expert to look at an ear drum, while the plenoptic image of the ear drum is captured on the sensor array of the same otoscope.

In other embodiments, a plenoptic otoscope system may include a set of detachable tips. Each detachable tip includes a different filter module. Each filter module may be used for a different purpose. For example, one filter module may be used for spectral imaging, while another filter module may be used for depth imaging. These detachable tips can be exchanged with one another, and are also referred to interchangeable tips. When a detachable tip is attached to the otoscope, the filter module included in that detachable tip is positioned at the entrance pupil of the primary imaging system.

The plenoptic otoscopes described can be designed and manufactured as original plenoptic instruments. Alternately, existing otoscopes can be modified to become plenoptic. In one embodiment, an after-market plenoptic conversion kit may be used to convert a conventional digital otoscope to a plenoptic digital otoscope. The conversion kit includes a plenoptic sensor with a microimaging array and a sensor array. The digital otoscope is equipped with a conventional sensor. During the conversion, the plenoptic sensor replaces the conventional sensor, such that the microimaging array (e.g., a microlens array or a pinhole array) is positioned at an image plane of the digital otoscope. For example, the microimaging array may be positioned at the plane where the conventional sensor was previously located.

FIGS. 9-16 provide additional description about the operation of a plenoptic otoscope and the use of plenoptic data (i.e., plenoptic images) for medical diagnosis. Plenoptic data of the ear canal can be processed to extract information about objects in the ear canal, especially three-dimensional and spectral information. Examples include the following:

Depth map estimation of the ear canal, including the TM
Depth map processing to extract three-dimensional information of the ear canal including the TM
TM shape estimation and classification
Three-dimensional ear canal segmentation, occlusion detection, object ordering, feature extraction and feature processing for classification of (medical) conditions of the ear
Three-dimensional ear-canal and TM visualization
Spectral measurement
Opacity/translucency Further aspects include use of plenoptic data to extract object information, optionally including displaying results of object information to a user, such as:

Shape of the TM
Obstruction by other objects
Selection of object obstructed by another object
Multi-view/multi-focal rendering of ear canal
Image rendering with different synthetic aperture size
Removal of occlusions in the view of the ear canal Data acquired with a plenoptic otoscope can contain volumetric data of the ear canal and can also provide spectral measurement as well as polarization states of objects. Enhanced imagery such as a depth map, disparity map, spectral images, polarization images and images showing the translucency of objects can be computed from the plenoptic data. In addition, higher-level information such as deformation of the shape of the TM, focusing on a selected object, and segmentation of the objects in the ear canal with respect to depth in the ear canal can also be performed. Results may be displayed to the user.

Consider first depth estimation. Given the design of a plenoptic otoscope, the data obtained with that system during a single data acquisition step can be processed to provide enhanced imagery with depth measurements of the TM as well as the ear canal at sub-millimeter resolution. These measurements can be used to aid the assessment of a medical condition.

Figure 9:
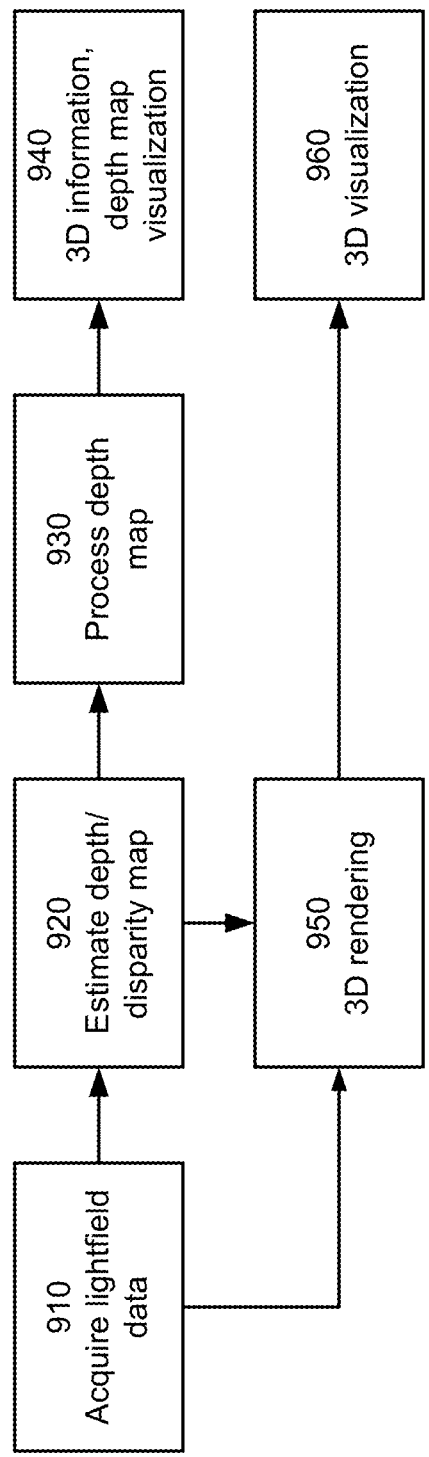
FIG. 9 is a flow diagram of depth estimation and three-dimensional information extraction from plenoptic otoscope data.

FIG. 9 is a flow diagram of depth estimation and three-dimensional information extraction from plenoptic data. A plenoptic otoscope acquires 910 a lightfield, which is a set of pixels that can be re-arranged into a set of images of the ear canal, where each image captures the ear canal from a different viewpoint (different viewing angle). These images, sometimes called multiviews, carry information about the three-dimensional shape of the ear canal and the objects inside it. However, this information is not captured explicitly, but is estimated from the multiviews using depth estimation techniques.

An example of a method to estimate depth imagery from a lightfield is described in U.S. patent application Ser. No. 14/064,090, "Processing of light fields by transforming to scale and depth space," which is incorporated by reference in its entirety herein. It is a multi-scale depth estimation approach, which analyzes the 4D lightfield data and can find a dense disparity map with sub-pixel precision. The method is based on extrema localization in light field scale and depth spaces, which are constructed by convolving a two-dimensional spatio-angular slice of a given 4D lightfield with a kernel designed to represent the structure of lightfields and to provide a simple way of estimating disparity values for the imaged object. Disparity values can then be converted to depth using a mapping based on system modeling.

Other methods for depth estimation can also be used. For example, multi-view stereo depth estimation algorithms can be applied. These include algorithms that pose the depth estimation problem as an energy minimization problem, where the energy includes a data fidelity term and a depth map smoothness term. The energy function can then be optimized using methods such as graph cuts, belief propagation, total variation, semi-global matching, etc. Sometimes image segmentation can be used in combination to depth estimation, in order to improve the final depth accuracy. Another approach that can be applied exploits the structure of the lightfield to obtain dense depth maps. An example of such a method is an algorithm that computes the structure tensor of the light field slices and uses that as a data fidelity term, while using total variation as a smoothness term. Computationally efficient methods based on normalized cross-correlation can also be applied to obtain a coarse depth map.

Yet another approach is described in U.S. patent application Ser. No. 14/312,586, "Disparity estimation for multiview imaging systems," which is incorporated by reference in its entirety herein. This estimates a depth/disparity map using multiple multiview images and taking advantage of the relationship between disparities for images taken from different viewpoints.

Depth estimation techniques are used to obtain 920 enhanced imagery (in this case, depth/disparity maps) of the ear canal and/or objects inside it from lightfields obtained with a plenoptic otoscope. Moreover, depth map information can also be used to extract other diagnostic data, such as relevant three-dimensional shape information about the ear canal, ear drum or other objects in the ear canal, in order to help in three-dimensional visualization and diagnosis of medical conditions of the ear (e.g., variants of otitis media). The depth measurements preferably are taken with respect to the front of the camera and are available for different spatial locations in the scene. They can be also calculated for objects in the field of view of the camera (e.g., the eardrum or the mallus).

Depth map processing 930 includes different methods for extraction of relevant three-dimensional diagnostic data of the ear canal, ear drum and/or other objects in the ear canal. For example, the curvature of the ear drum can be estimated from the depth map data, by fitting one-dimensional or two-dimensional polynomials to the depth map values. Using the curvature estimate we can classify the shape of the eardrum into bulging, neutral or retracting (convex, planar or concave). Moreover, we can evaluate the amount of bulging or retracting of the ear drum. This can be used to aid in medical diagnosis. For example, see the "Position" row of Table 1 above.

Figure 10:
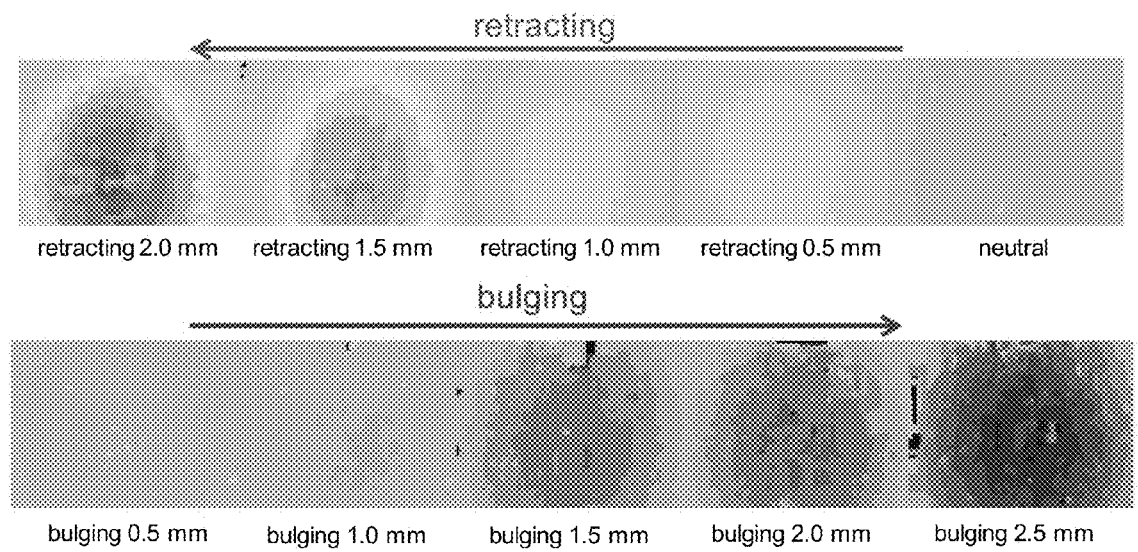
FIG. 10 shows depth maps estimated from plenoptic data imaging an ear trainer.

FIG. 10 shows estimated depth maps obtained from plenoptic lightfield images of an ear trainer, where bulging/retracting was simulated by injecting liquid into a membrane mounted on an eardrum cartridge. The different depth maps vary from retracting 2.0 mm, through neutral, to bulging 2.5 mm. In FIG. 10, the hotter colors (e.g., red) indicate that the eardrum is at a larger depth (i.e., farther away). The cooler colors (e.g., blue) indicate that the eardrum is at a smaller depth (i.e., closer).

Figure 11A:
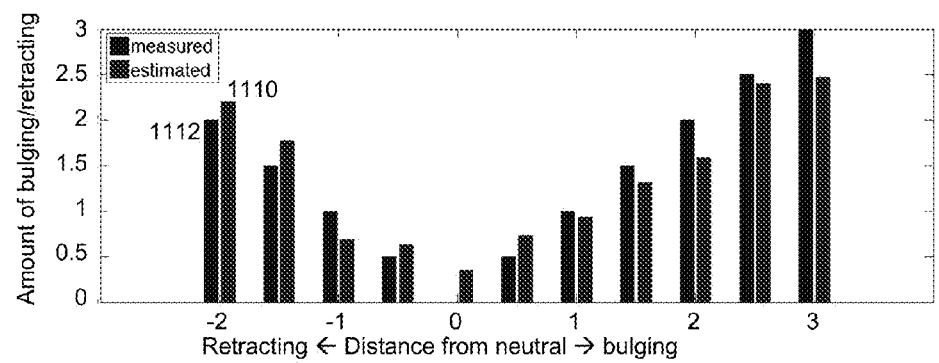
FIGS. 11a-b are graphs showing estimates of eardrum bulging/retracting, based on the depth maps of FIG. 10.
Figure 11B:
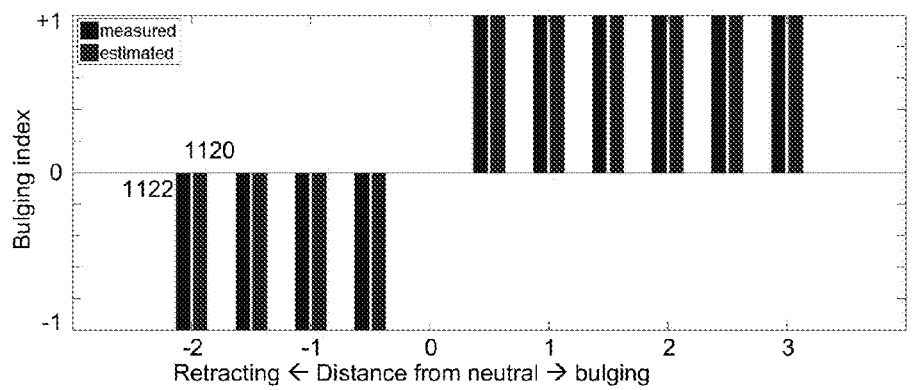

FIGS. 11a-b are graphs showing estimates of eardrum bulging/retracting, based on the depth maps of FIG. 10. FIG. 11a is a bar graph showing the estimating amount of bulging/retracting compared to the measured amount of bulging/retracting. The bar graph has pairs of bars for each eardrum position, where the right bar 1110 is the estimated amount based on the depth map and the left bar 1112 is the "ground truth" based on a direct measurement using a micrometer. The root mean square error is less than 0.3 mm. Depth resolution of less than 1 mm is achieved. Lightfields from the plenoptic otoscope can provide three-dimensional information of the eardrum with sub-millimeter precision.

In FIG. 11b, a "bulging index" is based on the estimated curvature of the eardrum. The curvature is estimated by fitting a second degree polynomial to one-dimensional scan lines through the depth map and then selecting the scan line with maximum curvature. In this example, a classifier is used to separate the data into three classes: bulging versus normal versus retracting. A bulging index of −1 means the eardrum is retracting, +1 means the eardrum is bulging, and 0 means the eardrum is neutral. The right bar graph 1120 in each pair is the estimated index and the left bar graph 1122 in each pair is the measured index. The estimated index is 100% accurate. Other classification algorithms may be used as well.

The depth measurements and classification results can be used to assist a human to make a diagnosis. Alternately, it may be used, possibly in combination with other data, to make an automated diagnosis.

FIGS. 10-11 show one example of depth map processing. Other types of depth map processing 930 include object segmentation, occlusion detection and estimation of object ordering, three-dimensional keypoint/feature extraction, three-dimensional feature description, classification based on three-dimensional feature descriptions, three-dimensional object measurements, comparisons with previous depth maps to obtain treatment progress evaluation, etc.

Figure 12A:
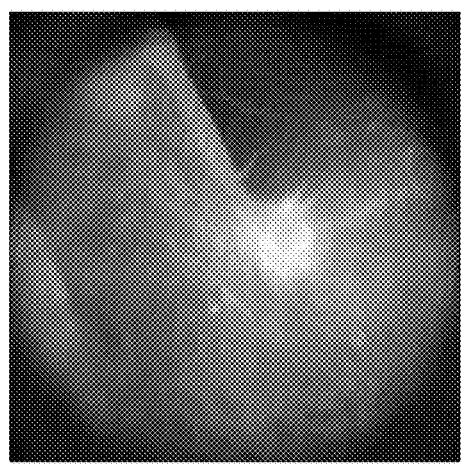
FIGS. 12a-c illustrate estimation of a depth map for an adult TM.
Figure 12B:
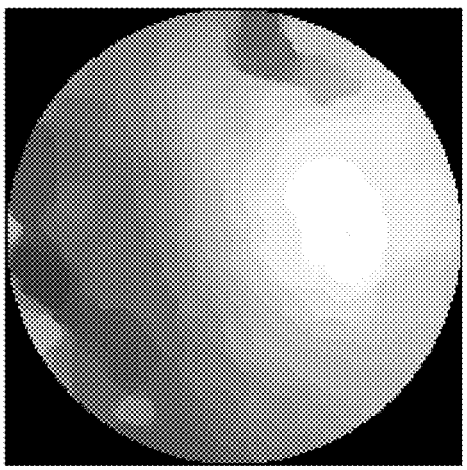
Figure 12C:

FIGS. 12a-b illustrate estimation of a depth map for an adult TM. FIG. 12a is an image showing the center view extracted from the lightfield data. It shows the TM and the malleolus (bone in the middle ear). FIG. 12b shows a depth map obtained from the plenoptic data using the method described above. The darker pixels denote closer distances (smaller depth) and the lighter pixels denote farther distances (larger depth). FIG. 12c is a three-dimensional rendering of the depth map of FIG. 12b. The shape of the TM is retracted in this example.

Returning to FIG. 9, another aspect of three-dimensional imaging of the ear canal is the visualization of the three-dimensional information. This can be achieved, for example, by visualization of the estimated depth maps as images (with hotter-colder colors such as in FIG. 10). This is referred to as depth map visualization, as indicated in block 940 of FIG. 9. Another way to visualize the three-dimensional information of the ear canal is to map the color values to the depth point cloud obtained from the depth map and then do three-dimensional rendering 950 using a graphics engines. The result is a three-dimensional surface with color information that the doctor can rotate using the mouse or other computer interface. This is referred to as three-dimensional visualization 960.

Plenoptic data can also be used to compute a two-dimensional rendering of a selected focal plane, or a three-dimensional volumetric rendering of the ear canal taking advantage of multiple viewpoints. With such visualization, the medical professional can switch between different views of e.g. some hair or wax in the ear canal and the ear drum, or can switch between views of the ear drum from different viewpoints.

The problem of "seeing through" occlusions in the ear canal can be addressed by refocusing the lightfield data at a selected focal plane, and then rendering the image with a large synthetic aperture. The focal plane can be selected by the user in various ways. For example:

- Selecting the focal plane from a depth map (such as shown in FIG. 10) extracted from the lightfield data. The user might click on a point in the depth map to select the focal plane, or might click on a legend for the depth map to select the focal plane.
- Selecting the focal plane based on an object in a three-dimensional visualization of the lightfield data. The user might select an object, which in turn defines the desired focal plane.
- Conversely, the focal plane may be selected based on a depth plane or object (e.g., an occluding object) to be removed from the view.

The focal plane can also be calculated via an algorithm using prior knowledge of object locations in the ear canal, e.g. typical distance between otoscope speculum and TM. Once the focal plane of interest is selected, whether by the user or determined automatically, an algorithm can be used to refocus extracted multiview images at the desired focal plane and can render the output image with different aperture size.

Figure 13:
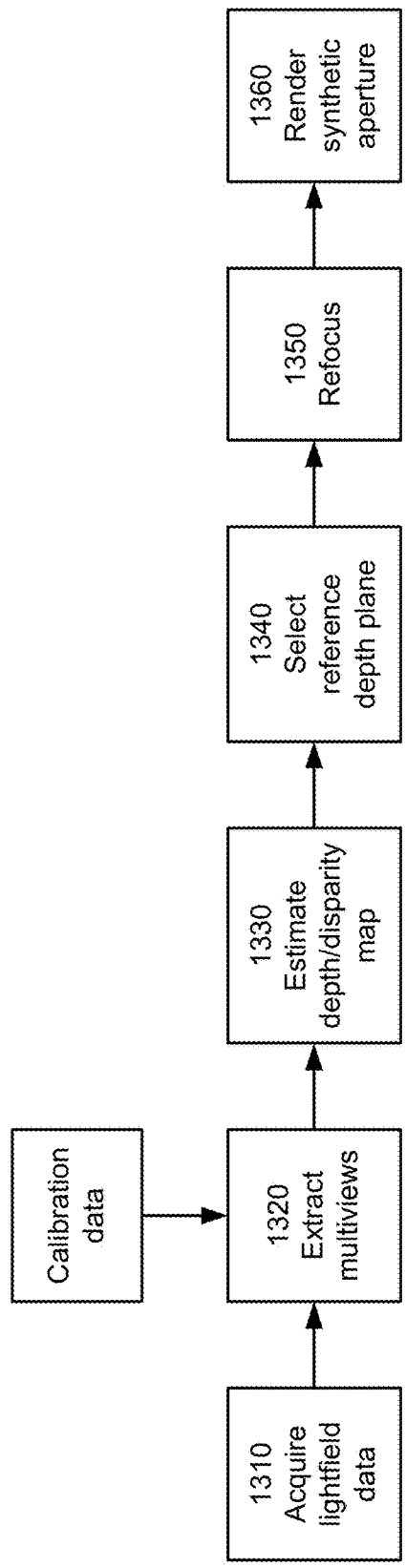
FIG. 13 is a flow diagram showing a method for selected focal plane rendering.
Figure 14:
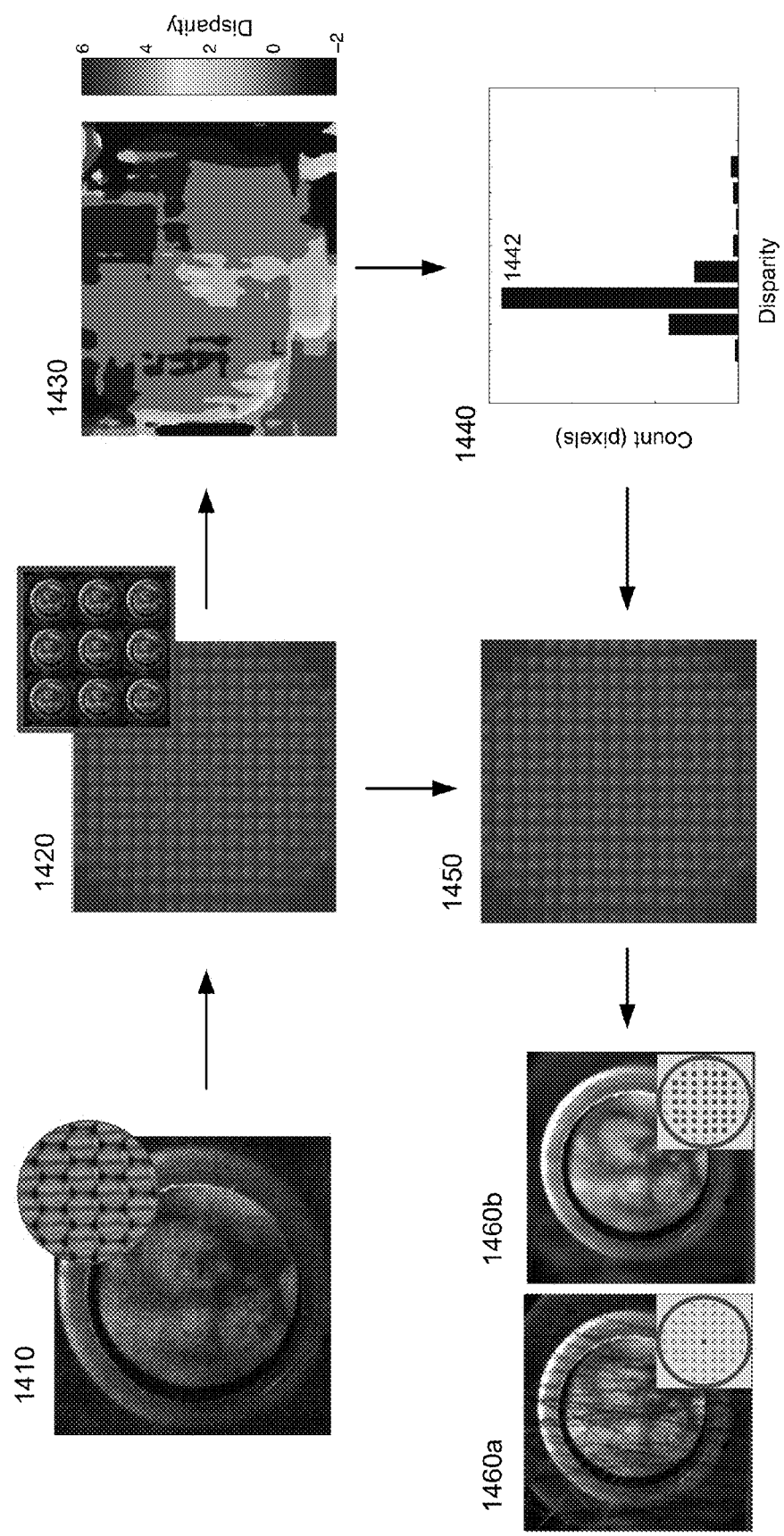
FIG. 14 shows images corresponding to the flow diagram of FIG. 13.

FIG. 13 is a flow diagram showing a method for selected focal plane rendering. This method is illustrated using an example simulation shown in FIG. 14. This example renders the image at the focal plane of the TM while removing obstructing hair in front of the TM. A plenoptic otoscope acquires 1310 plenoptic data of the ear canal. Image 1410 shows the raw sensor data. This data includes multiple views, but the views are interleaved with each other. Multiple views of the ear canal are extracted 1320 from the lightfield data. FIG. 14 shows the multiple views 1420 of the ear canal. This looks like an array of identical images, but the images are not identical. Each image is taken from a different view. The location of the image within the array indicates the viewpoint from which the image was taken.

A disparity map is calculated 1330 from the different views. In this example, not all the views are used to calculate the disparity map. Rather, the disparity map is calculated from selected views. The views can be selected by algorithm, or can be selected by the user. FIG. 14 shows a disparity map 1430 for the image. Given the configuration of the plenoptic otoscope, there is a one-to-one mapping between disparity and depth. Therefore, the disparity map is a form of depth map, and vice versa. The disparity map is calculated according to:

$$\hat{n}_p(x,y) = \arg\max\{\text{corr}(I_1, \ldots, I_N)\} \quad (1)$$

where $\hat{n}_p(x,y)$ is the estimated disparity at pixel (x,y), $I_1 \ldots I_N$ are the translated images, and corr is a correlation computation operator. The correlation can be calculated either globally or locally by using a sliding window. Different types of correlation computations can be used, such as sum of absolute different, normalized cross correlation, multiplied eigenvalues of covariance matrix, phase correlation, etc. Further description is given in U.S. patent application Ser. No. 14/312,586, "Disparity estimation for multiview imaging systems," which is incorporated by reference in its entirety herein.

The disparity value assigned to the highest number of pixels in the image is determined. In this example, that disparity value corresponds to a depth plane that is chosen 1340 as the reference plane. A histogram 1440 of number of pixels at different disparities is shown in FIG. 14. The disparity of 0 has the largest number of pixels (bar 1442) and is therefore selected as the reference plane. The plenoptic data is used to refocus 1350 the image at the reference plane, as depicted by the multiviews 1450.

In this example, a synthetic aperture image 1460 is created 1360 by averaging shifted (i.e., disparity-corrected) multiview images. Different number of views can be used in the averaging process to render the output image with different synthetic apertures. In this example, the synthesized image $I_s$ is computed as a weighted average of the views, according to:

$$I_S = (\Sigma w_i V_i')/(\Sigma w_i) \quad (2)$$

$V_i'$ is the ith view after shifting to account for disparity. The image shift could be done in the spatial domain or in the frequency domain. $w_i$ is a weighting factor, for example to compensate for non-uniformity such as due to vignetting. The summation is over the number of views used to construct the synthesized image. FIG. 14 shows two synthesized images 1460a and 1460b.

Figure 15C:
FIG. 15c shows a reference image captured without any hair occlusions.
Figure 15B:
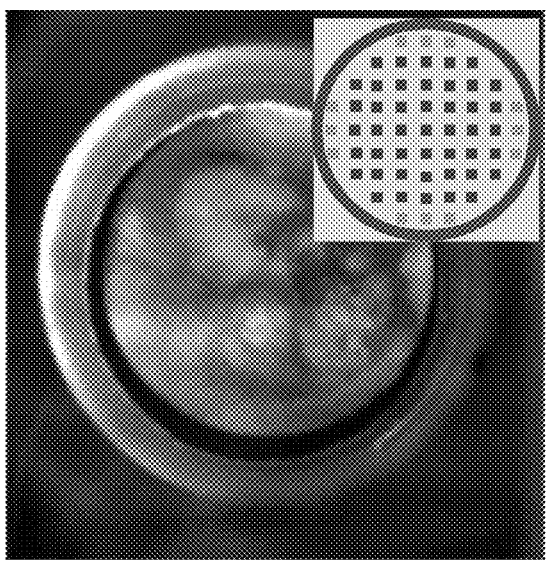
FIGS. 15a-b show image rendering at a selected focal plane with a small synthetic aperture and with a large synthetic aperture, respectively, to remove hair occlusions.
Figure 15A:
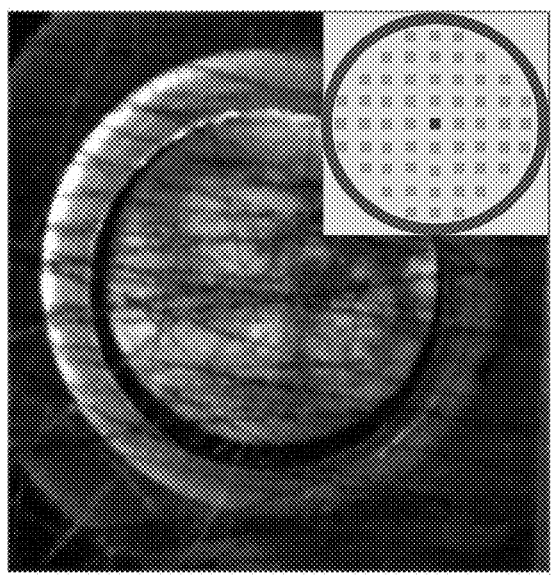
Figure 16A:
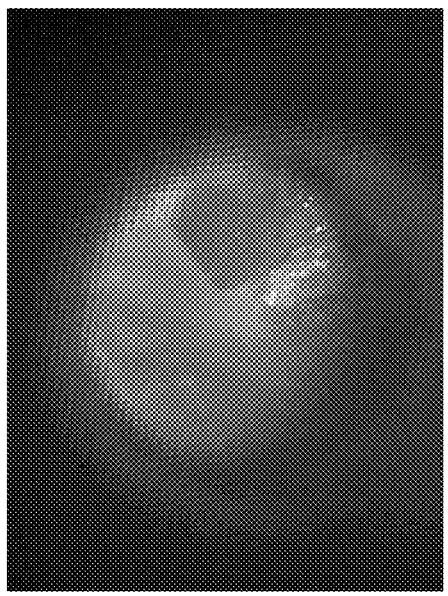
FIGS. 16a-d show spectral images captured by a plenoptic otoscope.
Figure 16B:
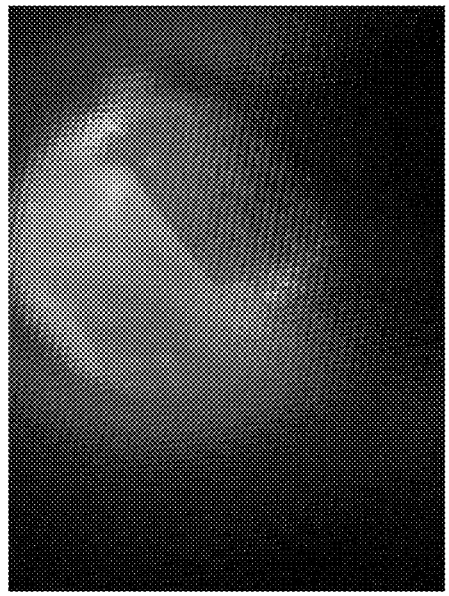
Figure 16C:
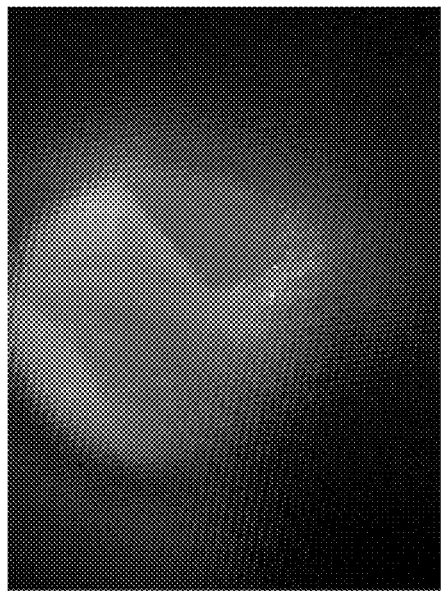
Figure 16D:
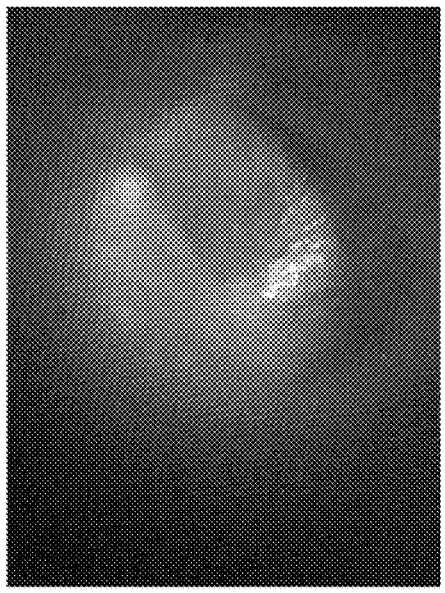

FIG. 15a shows a synthesized image using a small aperture. FIG. 15b shows the synthesized image using a large aperture. In the large aperture example, all the views were included in the averaging process. It is also possible to select views to be included in the rendering according to an algorithm. Both images in FIGS. 15a and 15b are for a scene with hair occlusions. FIG. 15c shows a reference image for comparison. This reference image is without hair occlusions. The multiviews of FIG. 15b significantly reduce the amount of hair occlusion compared to the smaller aperture of FIG. 15a.

Spectral responses of tissue or the TM can be measured by using spectral narrow- or wide bandpass filters in the plenoptic otoscope. With such spectral measurements, a characterization of the properties of the TM, such as translucency or coloration, can be obtained in conjunction with depth measurements. Spectral measurements can be obtained for selected locations in the scene, e.g. on the TM. When choosing a near infrared (NIR) filter, longer wavelengths are penetrating the object at deeper layers, making it, e.g. possible to obtain characterization of objects behind semi-translucent objects (e.g., behind the TM).

Spectral measurements of the ear canal can be obtained when inserting a spectral filter array into the lightfield otoscope. Examples are described above with respect to FIGS. 5-6. The lightfield data obtained from the sensor contain three-dimensional location as well as wavelength specific information. The spectral filters can be chosen such that they capture spectral measurements of the ear canal with wide-band filters as used in conventional color imaging, and with narrow-band filters that capture certain specific information that is typically invisible to the human eye, e.g. certain type of amber coloration. When NIR filters are used, objects behind translucent object layers can be imaged, since NIR light travels deeper through tissue before being reflected. The user will obtain information of spectral reflectance of objects in the ear canal as well as a characterization of translucency of objects.

FIGS. 16a-d show spectral images captured by a plenoptic otoscope. This example uses four different wavebands: red, green, blue and amber. The images are obtained using a lightfield otoscope that has a filter module with four filters multiplexed in the aperture plane. FIGS. 16a-d are the red, green, blue and amber images, respectively.

Referring again to Table 1 above, the three conditions of the ear shown in Table 1 are different and they can be distinguished from one another based on one or more of the following features: color, position (e.g., 3D shape), and translucency. In order to make correct diagnosis of the ear condition, a plenoptic otoscopic can be used to capture accurate information about color, three-dimensional shape and/or translucency of an inside of an ear (e.g., a tympanic membrane in an ear canal). These spectral measurements, individually or together with depth, polarization, translucency and/or bulging estimation, might be input to a machine learning algorithm to classify different medical conditions. The trained machine may be used to aid or automate diagnosis.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A method for making a medical diagnosis of an ear interior, comprising:
   acquiring plenoptic data of a tympanic membrane, the plenoptic data comprising multiviews of the tympanic membrane captured from different viewing angles, the multiviews captured simultaneously by a plenoptic otoscope imaging the tympanic membrane; and
   combining, by a computer system, the multiviews of the plenoptic data to produce enhanced imagery of the tympanic membrane, the enhanced imagery including at least one of a depth map of the tympanic membrane and a set of different spectral images of the tympanic membrane derived from the plenoptic data; and
   displaying diagnostic data based on the enhanced imagery, the diagnostic data used in medical diagnosis of the ear interior.

2. The method of claim 1 further comprising:
   processing, by the computer system, the diagnostic data to make the medical diagnosis.

3. The method of claim 1 wherein the diagnostic data includes the enhanced imagery.

4. The method of claim 1 wherein the enhanced imagery includes a depth map of the tympanic membrane.

5. The method of claim 4 wherein the depth map has sub-millimeter resolution.

6. The method of claim 4 wherein processing the plenoptic data to produce the depth map of the ear interior comprises:
   processing the plenoptic data by transforming to a scale and depth space.

7. The method of claim 4 further comprising:
   displaying, by the computer system, a visualization of the depth map of the tympanic membrane, the visualization used by a human in medical diagnosis of the ear interior.

8. The method of claim 1 wherein the diagnostic data includes three-dimensional information about the tympanic membrane, the three-dimensional information derived from the enhanced imagery.

9. The method of claim 8 wherein the three-dimensional information includes whether the tympanic member is bulging or retracting.

10. The method of claim 1 wherein the enhanced imagery includes different spectral images of the tympanic membrane.

11. The method of claim 10 wherein the spectral images include an amber or yellow image.

12. The method of claim 1 wherein the enhanced imagery includes images showing translucency of the tympanic membrane.

13. The method of claim 1 wherein the enhanced imagery is produced for a selected reference plane.

14. The method of claim 13 wherein the reference plane is selected based on features in the tympanic membrane.

15. The method of claim 1 wherein combining the multiviews of the plenoptic data reduces occlusions.

16. The method of claim 1 wherein the medical diagnosis is otitis media.

* * * * *